(12) United States Patent
Yokoyama et al.

(10) Patent No.: US 6,541,205 B1
(45) Date of Patent: Apr. 1, 2003

(54) METHOD FOR ASSAYING NUCLEIC ACID

(75) Inventors: Akihiro Yokoyama, Kanagawa (JP);
Takahiko Ishiguro, Kanagawa (JP);
Juichi Saitoh, Kanagawa (JP)

(73) Assignee: Tosoh Corporation, Tokyo (JP)

( * ) Notice: Subject to any disclaimer, the term of this patent is extended or adjusted under 35 U.S.C. 154(b) by 0 days.

(21) Appl. No.: 09/576,537

(22) Filed: May 23, 2000

(30) Foreign Application Priority Data

May 24, 1999 (JP) .......................................... 11-143854

(51) Int. Cl.[7] .......................... C12Q 1/68; C12P 19/34; C07H 21/04; C07H 21/02
(52) U.S. Cl. ........................ 435/6; 435/91.1; 435/91.2; 435/91.21; 435/91.5; 435/91.51; 536/23.1; 536/24.3; 536/24.33
(58) Field of Search ....................... 435/91.2, 6, 91.1, 435/91.5, 91.51, 91.21; 536/24.2, 24.1, 24.3, 23.1, 24.33

(56) References Cited

FOREIGN PATENT DOCUMENTS

| EP | 0 855 447 | * | 7/1998 |
| EP | 0 969 101 | * | 1/2000 |
| WO | WO 91/04340 | * | 4/1991 |

* cited by examiner

Primary Examiner—Kenneth R. Horlick
Assistant Examiner—Cynthia Wilder
(74) Attorney, Agent, or Firm—Jeffrey I. Auerbach; Liniak, Berenato & White

(57) ABSTRACT

A method for assaying a target nucleic acid, comprising: providing an RNA amplification system comprising producing a double-stranded DNA using, as a template, a target RNA containing a specific nucleotide sequence in a sample, said double-stranded DNA having a promoter sequence and being capable of transcribing an RNA comprising the specific nucleotide sequence or a sequence complementary to the specific nucleotide sequence, producing an RNA transcription product comprising the specific nucleotide sequence or a sequence complementary to the specific nucleotide sequence in the presence of an RNA polymerase, and producing the double-stranded DNA using the RNA transcription product as a template, in the presence of a probe labeled with an intercalating fluorochrome having a sequence complementary to the RNA transcription product; measuring the fluorescence intensity in the RNA amplification system with time; calculating a time when the fluorescence intensity satisfies a prescribed criterion based on the measured change in the fluorescence intensity with time; and determining a concentration of the target nucleic acid in the sample based on the calculated time.

10 Claims, 5 Drawing Sheets

METHOD FOR ASSAYING NUCLEIC ACID

BACKGROUND OF THE INVENTION

1. Field of the Invention

The present invention relates to a method for qualitatively or quantitatively analyzing a target RNA having a specific nucleotide sequence, which is considered to be contained in a gene mixture of DNA, RNA, or the like, and the method is useful in the field of clinical diagnoses, such as gene diagnosis and the like. Also, the present invention relates to a method for qualitatively or quantitatively analyzing microorganisms in environments, such as foods, indoors, soils, rivers, ocean, and the like.

2. Discussion of the Background

Generally, a high specificity and a high sensitivity are required for an assay of biological components. An assay of a nucleic acid having a specific nucleotide sequence (target nucleic acid) can use a property that the nucleic acid sequence-specifically forms a complex with another nucleic acid having a sequence complementary to the specific nucleotide sequence (nucleic acid probe).

When the target nucleic acid having a specific nucleotide sequence is assayed, a means for obtaining a measurable signal related to the amount of the formed complex is important. Furthermore, the amount of the target nucleic acid which can be present in a sample is extremely small for a purpose of clinical diagnosis etc. so that such a means requires a step for amplifying the extremely small amount of the nucleic acid.

In diagnosis of viral infection, since the amount of a target nucleic acid (viral nucleic acid) in a clinical sample is often extremely small, a polymerase chain reaction (PCR), particularly a competitive PCR, is known as a means for obtaining a high sensitivity by improving the signal strength in order to realize the measurement with high sensitivity and good reproducibility. In this method, PCR is carried out by adding a competitor (a different nucleic acid sequence having a primer recognizing region common to the target nucleic acid) having a known concentration to a sample, and the concentration of the target nucleic acid in the sample is estimated by comparing amplified degrees between the competitor and the target nucleic acid. More specifically, a nucleic acid having a sequence complementary to a primer on its terminus and can be distinguished from the amplified product of the target nucleic acid by a separation means, such as electrophoresis or the like (e.g., based on a different chain length) is prepared, this nucleic acid is added to a sample to give respective concentrations, and PCR of these mixtures is simultaneously carried out.

Additionally, an assay method in a homogenous system has been proposed as a method for assaying a target nucleic acid using PCR. For example, an assay method has been proposed, in which PCR is carried out in the presence of an intercalating fluorochrome, the fluorescence of the reaction solution is measured in each PCR cycle, and the initial amount of the target nucleic acid is determined based on its changes (JP-A-5-237000 (the term "JP-A" as used herein means an "unexamined published Japanese patent application"); Igaku-no Ayumi, 173(12): 959–963 (1995); Analytical Biochemistry, 229: 207–213 (1995)). In this assay method, the amplified product by PCR is a double-stranded DNA so that an intercalating fluorochrome having a property to change its fluorescence characteristic, such as an increase in the fluorescence intensity by intercalation into the double-stranded nucleic acid, is used, the fluorochrome is added to the reaction solution in advance before amplification operation by PCR, the fluorescence intensity in the reaction solution is measured with time, and the initial amount of the target nucleic acid is determined, for example, based on its build up cycle etc.

On the other hand, NASBA method and 3SR method are also known as RNA amplification methods. In these methods, a double-stranded DNA fragment containing a promoter sequence is synthesized for a target RNA using a primer containing the promoter sequence, a reverse transcriptase and ribonuclease H, an RNA containing a specific nucleotide sequence of the target RNA is synthesized in the presence of an RNA polymerase, and then a chain reaction is carried out in which the RNA is subsequently used as the template for the synthesis of the double-stranded DNA containing the promoter sequence. Thereafter, the reaction is completed when the RNA is amplified, and the amplified RNA is determined by an electrophoresis method or a hybridization method using a labeled nucleic acid probe.

In the hybridization method using a labeled nucleic acid probe, a nucleic acid probe labeled in such a manner that it generates a measurable signal, such as visible light, fluorescence, emission, or the like, forms a complex with a target nucleic acid, and then unreacted nucleic acid probe is washed or degraded, and the label is measured to assay the target nucleic acid. A method called sandwich assay is generally known, which uses two probes each comprising a sequence capable of forming a complementary bond with a specified sequence at different region in a specified nucleic acid. In this method, a first probe is immobilized on an insoluble carrier, and a part of a second probe is labeled with a dye having a color in the visible region, a fluorescent material, or an enzyme capable of forming them. Then, these probes are added to a sample, a specified nucleic acid in the sample is complementary bound to the first and second probes, and a complex composed of these three materials is formed on the insoluble carrier. Subsequently, the resultant supernatant in the sample reaction solution is separated from the insoluble carrier to separate the free second probe (B/F separation step). Thereafter, the presence or absence and amount of the specified nucleic acid in the sample are determined by measuring the label in the complex on the insoluble carrier. Also, when an enzyme which can form a dye having a color in the visible region or a fluorescent material is used as the second probe, the free second probe is removed after the complex forming step, an enzyme substrate as the precursor is added to the sample reaction solution, and then the presence or absence and amount of the target nucleic acid in the sample are determined by, measuring the dye or fluorescent material which is the reaction product.

Since the sandwich assay uses an insoluble carrier in the reaction solution, the second probe is nonspecifically adsorbed on the insoluble carrier. Accordingly, when the label in the complex on the insoluble carrier is measured, an error occurs in the measured results due to the presence of the label of the second probe nonspecifically adsorbed on the insoluble carrier. Thus, a problem is occurred when the presence or absence and amount of the specified nucleic acid in the sample are determined. Particularly, since the diagnosis of viral infection requires detection of an extremely small amount of viral nucleic acid in a clinical sample with a good reproducibility and a high sensitivity, the problem caused by nonspecific adsorption is an important problem to be solved.

In order to avoid this problem, various attempts are made, such as hydrophilic treatment of the surface of the insoluble carrier, blocking of adsorption points of the carrier surface with a protein etc., sufficiently washing of the insoluble carrier after the B/F separation step, and the like.

However, in the chemical hydrophilic treatment of the carrier surface, its result depends on the material of the carrier, and it is not always easy technically. Also, in the method in which the carrier surface is coated with a protein in order to block adsorption points on the carrier surface in advance, there is a possibility that the protein interacts with the nucleic acid moiety or label of the second probe to cause additional nonspecific adsorption on the carrier. Additionally, in the B/F separation step, there is an operational limitation in increasing the number of times of washing. Thus, for example, when a surfactant is added to the washing solution, degradation of the complex formed on the carrier may be accelerated.

In the competitive PCR method, in order to assay one test sample, it is necessary to prepare a competitor having various concentrations including an assumed nucleic acid concentration and carry out PCR of a sample to which the competitor has been added. Additionally, an separation operation, such as electrophoresis or the like, must be carried out by taking out the sample from the reaction container after completion of PCP. Accordingly, it is inadequate to applying it to clinical tests in which a large number of samples must be treated quickly and conveniently. Also, since the sample must be taken out from the reaction solution, a problem of causing a pseudopositive reaction due to scattering of the amplified product cannot be solved. Additionally, when the target is RNA, so-called RT-PCR in which PCR is carried out after once synthesizing a cDNA using the RNA as the template in the presence of a reverse transcriptase must be carried out so that it is necessary substantially to carry out two stage steps.

In the method in which PCR is carried out in the presence of an intercalating fluorochrome, its principle is intercalation into a double-stranded nucleic acid. Accordingly, when double-stranded DNAs contaminant other than the specified nucleic acid, such as a large amount of genomic DNA and the like, are present in the test sample, the intercalating fluorochrome is also intercalated into them to cause a problem of generating a large background. Also, in the PCR method, a pair of complementary oligonucleotides of the specified nucleic acid sequence are used as elongation reaction primers, but they mutually form a complementary bond depending on the primer sequences and, as a result, sometimes produce a primer dimer mutually using the other primer as the template. Since the intercalating fluorochrome nonspecifically intercalates into double-strands, it also causes a problem in that the background increases due to the production of such a dimer.

When the NASBA method or 3SR method is used, it is possible to determine the amplified nucleic acid by an electrophoresis method or a hybridization method using a labeled nucleic acid probe after the reaction after amplification of the RNA to a sufficiently detectable amount. However, it is impossible to determine the target RNA originally present in the sample before the amplification. Also, when the electrophoresis method or the hybridization method using a labeled nucleic acid probe is carried out, there is a problem in that a pseudopositive reaction occurs due to scattering of the amplification product.

SUMMARY OF THE INVENTION

Accordingly, an object of the present invention is to provide a quick, convenient and highly accurate method for assaying a target RNA (single-stranded RNA) containing a specified nucleic acid sequence originally present in the sample, and particularly, to provide a method by which the entire operations can be completed in a closed container.

Specifically, the present invention relates to the following (1) to (7).

(1) A method for assaying a target nucleic acid, comprising:
providing an RNA amplification system comprising:
producing a double-stranded DNA using, as a template, a target RNA containing a specific nucleotide sequence in a sample, said double-stranded DNA having a promoter sequence and being capable of transcribing an RNA comprising the specific nucleotide'sequence or a sequence complementary to the specific nucleotide sequence;
producing an RNA transcription product comprising the specific nucleotide sequence or a sequence complementary to the specific nucleotide sequence in the presence of an RNA polymerase; and
producing the double-stranded DNA using the RNA transcription product as a template, in the presence of a probe labeled with an intercalating fluorochrome having a sequence, complementary to the RNA transcription product;
measuring the fluorescence intensity in the RNA amplification system with time;
calculating a time when the fluorescence intensity satisfies a prescribed criterion based on the measured change in the fluorescence intensity with time; and
determining a concentration of the target nucleic acid in the sample based on the calculated time (2) The method according to the above (1), wherein the time which satisfies a prescribed criterion is a time to reach a definite fluorescence intensity.

(3) The method according to the above (1), wherein the time which satisfies a prescribed criterion is a time when an increasing rate of the fluorescence intensity per unit of time becomes a maximum.

(4) The method according to any one of the above (1) to (3), wherein the concentration of the target nucleic acid is determined by comparing the time which satisfies a prescribed criterion with the times in at least two RNA samples containing the specific nucleotide sequence at a different concentration.

(5) The method according to the above (1), wherein, in the RNA amplification system,
a single-stranded DNA is produced in the presence of an RNA-dependent DNA polymerase using a primer having a sequence complementary to the specific nucleotide sequence and a primer having a homologous sequence of the specific nucleotide sequence, wherein one of the primers is a promoter primer having a promoter sequence of the RNA polymerase at the 5'-side, and using the target RNA as a template;
the double-stranded DNA is produced in the presence of a DNA-dependent DNA polymerase using the single-stranded DNA as a template;
the RNA transcription product is produced from the double-stranded DNA in the presence of a RNA polymerase; and
the RNA transcription product is subsequently used as the template for producing the single-stranded DNA in the presence of the RNA-dependent DNA polymerase.

(6) The method according to the above (1), wherein a complex formed by a complementary bond between the probe labeled with an intercalating fluorochrome and the RNA transcription product has a fluorescence characteristic different from the probe labeled with an intercalating fluorochrome which is not form a complex with the RNA transcription product.

(7) The method according to the above (1) or (6), wherein the probe labeled with an intercalating fluorochrome complementary bonds to the RNA transcription product so that the intercalating fluorochrome is intercalated between the produced RNA and the probe.

DETAILED DESCRIPTION OF THE INVENTION

Figure 1:
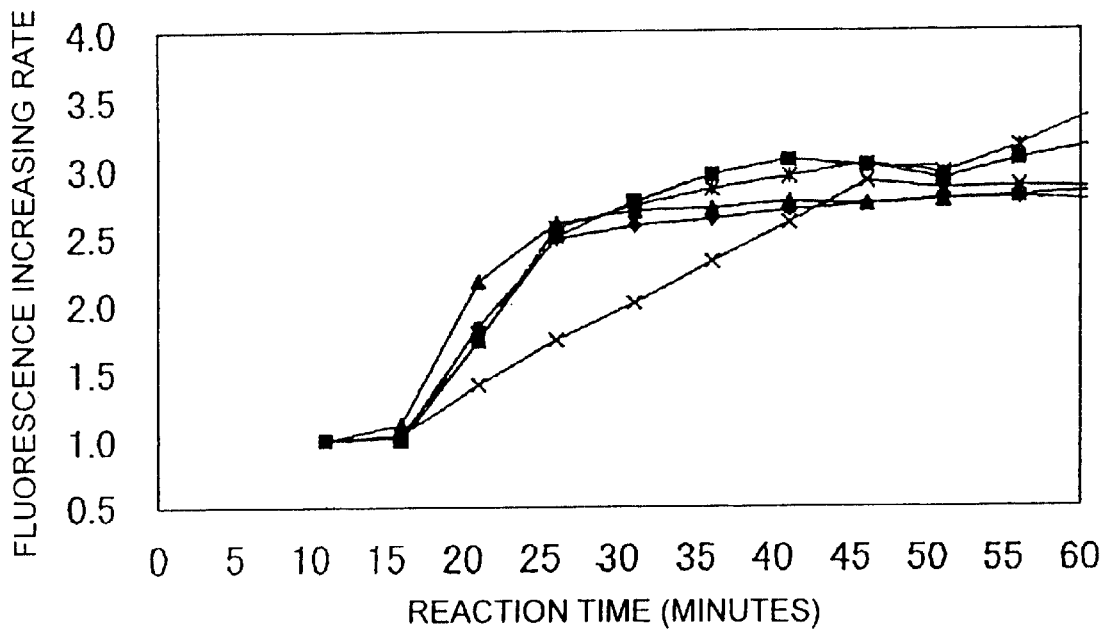
FIG. 1 is a graph showing a reaction time and a fluorescence increasing rate at a concentration of $10^9$ copies/tube (initial RNA amount) carried out in Example 1.
Figure 2:
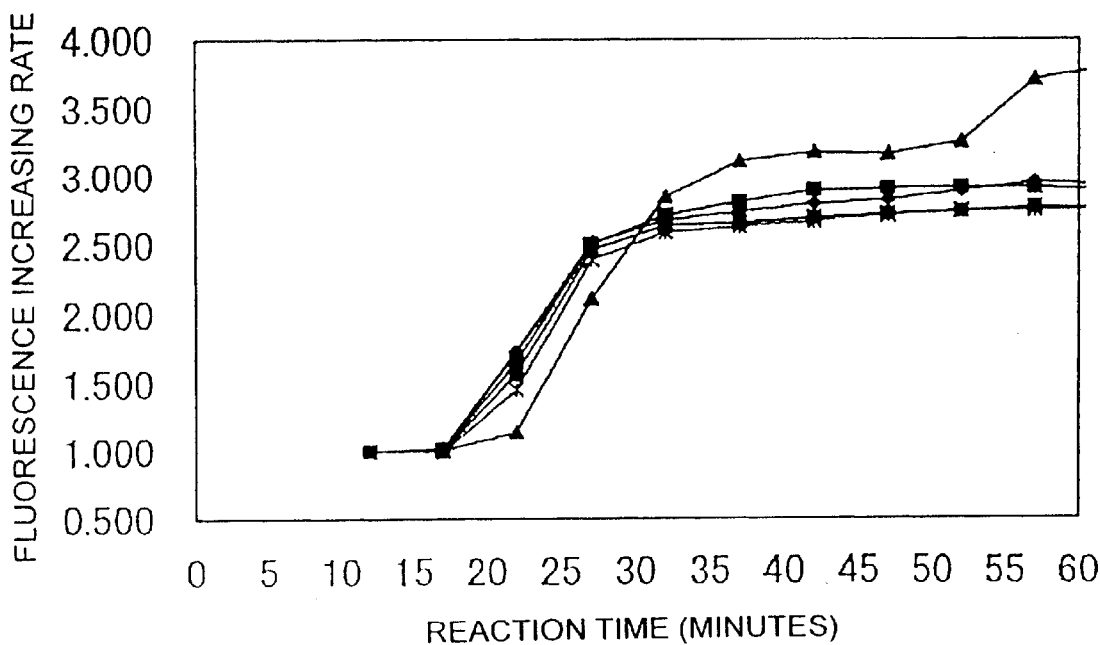
FIG. 2 is a graph showing a reaction time and a fluorescence increasing rate at a concentration of $10^8$ copies/tube (initial RNA amount) carried out in Example 1.
Figure 3:
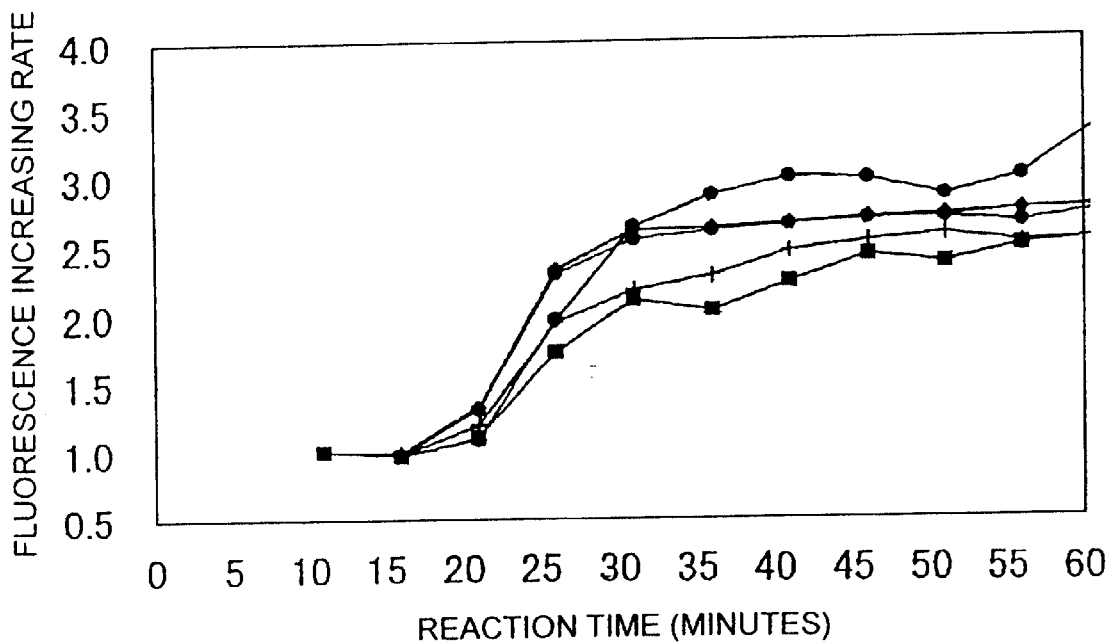
FIG. 3 is a graph showing a reaction time and a fluorescence increasing rate in at a concentration of $10^7$ copies/tube (initial RNA amount) carried out in Example 1.
Figure 4:
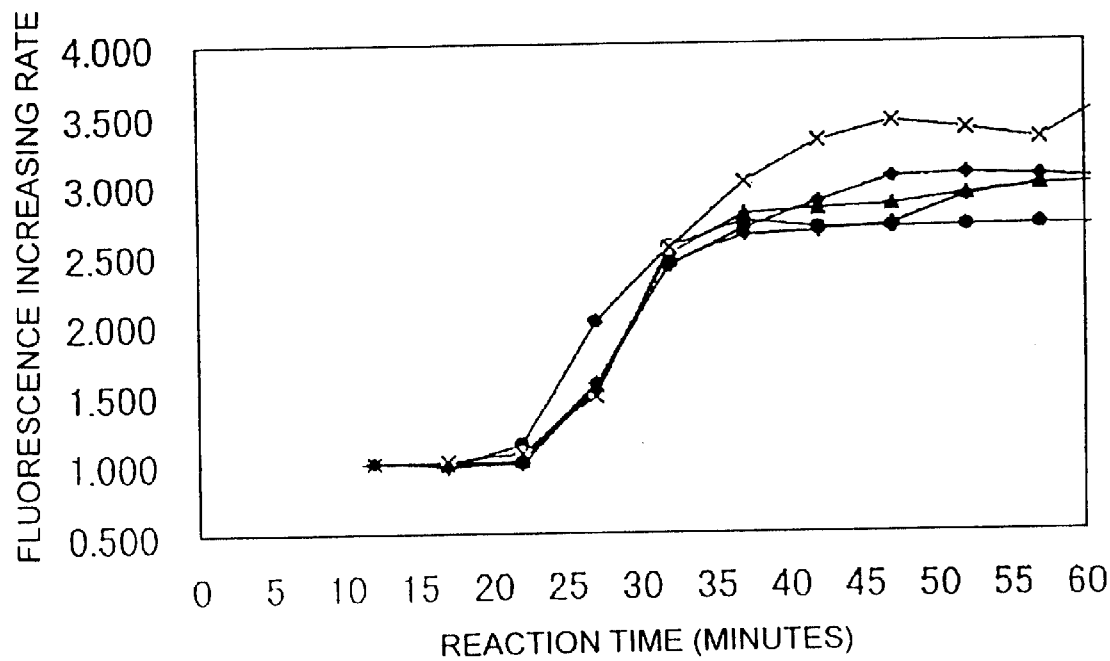
FIG. 4 is a graph showing a reaction time and a fluorescence increasing rate at a concentration of $10^6$ copies/tube (initial RNA amount) carried out in Example 1.
Figure 5:
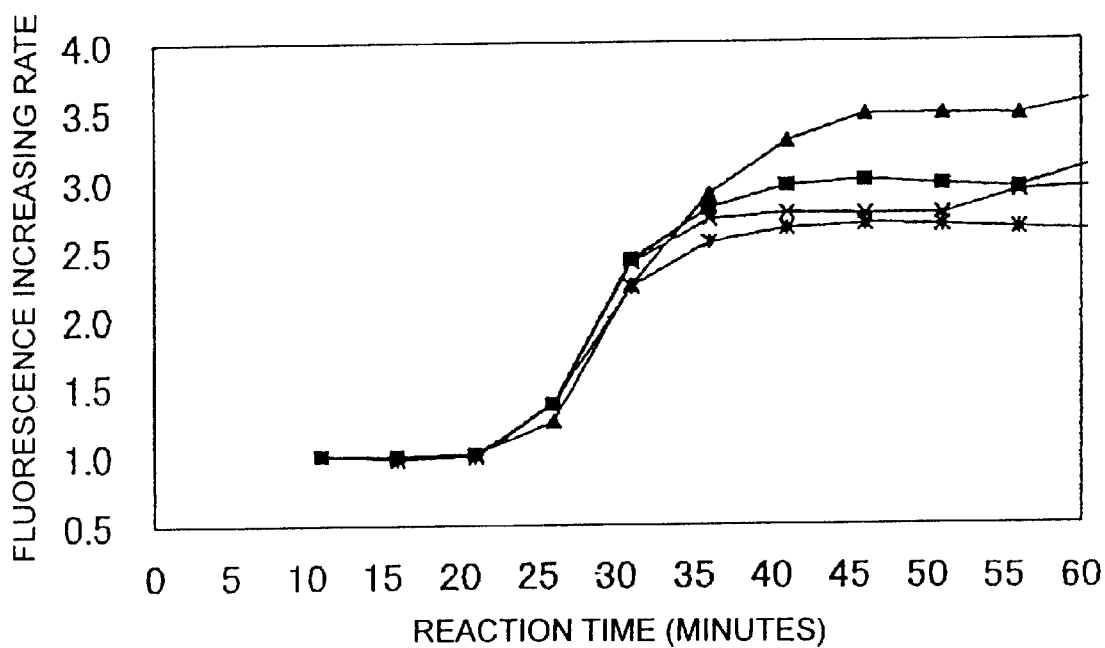
FIG. 5 is a graph showing a reaction time and a fluorescence increasing rate at a concentration of $10^5$ copies/tube (initial RNA amount) carried out in Example 1.
Figure 6:
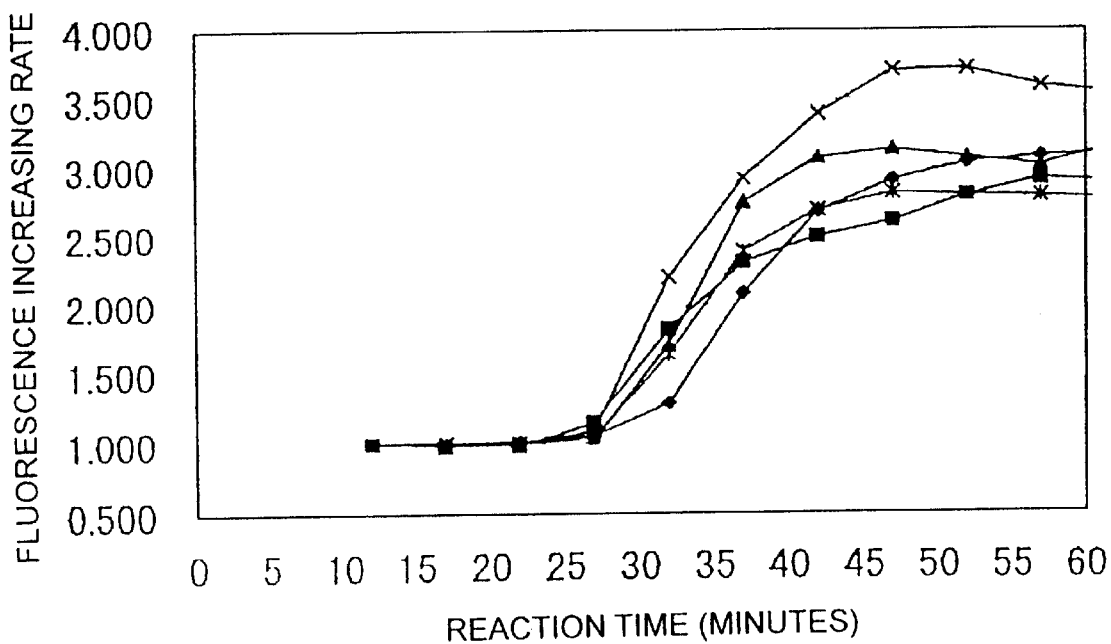
FIG. 6 is a graph showing a reaction time and a fluorescence increasing rate at a concentration of $10^4$ copies/tube (initial RNA amount) carried out in Example 1.

Some of the present inventors have developed a nucleic acid probe which has a nucleic acid sequence complementary to a specific nucleotide sequence of a target nucleic acid and is labeled with an intercalating fluorochrome in such a manner that a measurable fluorescence signal is generated when it is bound to the target nucleic acid (JP-A-8-211050; EP 714986; *Nucleic Acids Research*, 24(24): 4992–4997 (1996)). Since this nucleic acid probe generates a measurable fluorescence signal by forming a complementary bond with a target nucleic acid, the presence or absence of a complementary bond formation can be detected and the thus formed complementarily bonded complex can be assayed without separating a portion of the probe which does not form the complementary bond from the reaction system. Thereafter, the present inventors have found that assay of a target RNA originally present in a sample can be carried out, preferably in a closed system, by amplifying the RNA by the action of nucleic acid primers and a nucleic acid polymerase in the presence of this nucleic acid probe and analyzing a relationship between a fluorescence intensity and a time obtained by measuring the fluorescence intensity with time. Thus, the present invention has been accomplished.

The present invention provides a method for assaying a single-stranded RNA (target RNA) containing a specific nucleotide sequence in a sample. The term "assaying" as used herein means both to detect whether or not the RNA is present in a sample and to analyze the amount of the RNA originally existing in the sample.

The present invention includes an operation in which at least the following reagents (A) to (I) are prepared, and they are added to a sample presumably containing a target RNA successively, at least two thereof are added at a time, or all of them are added at a time (it is not necessary to add (A) to (I) in this order), and another operation in which a fluorescence signal is measured with time:

(A) a first single-stranded oligonucleotide having a sequence complementary to the 3'-end sequence of a specific nucleotide sequence in the target RNA;
(B) a RNA-dependent DNA polymerase;
(C) deoxyribonucleoside triphosphate;
(D) ribonuclease H or an enzyme having an equivalent RNA hydrolyzing activity;
(E) a second single-stranded oligonucleotide having (1) a promoter sequence of a DNA-dependent RNA polymerase, (2) an enhancer sequence of the promoter, and (3) a nucleotide sequence identical to the 5'-end sequence of the specific nucleotide sequence in the target RNA, in this order from the 5'-end side;
(F) a DNA-directed DNA polymerase;
(G) a DNA-dependent RNA polymerase;
(H) ribonucleoside triphosphate; and
(I) a third single-stranded oligonucleotide which has a sequence complementary to the specific nucleotide sequence and is labeled in such a manner that a measurable fluorescence signal is generated when bound to a nucleic acid having the same sequence.

In addition to the combination of the first, second and third single-stranded oligonucleotides of the reagent (A), reagent (E) and reagent (I), another combination of a first to a third single-stranded oligonucleotides of the following reagents (J) to (L) may also be used:

(J) a first single-stranded oligonucleotide having (1) a promoter sequence of a DNA-dependent RNA polymerase, (2) an enhancer sequence of the promoter, and (3) a sequence complementary to a 3'-end sequence of the specific nucleotide sequence in the target RNA, in this order from the 5'-end side;
(K) a second single-stranded oligonucleotide having a nucleotide sequence identical to the 5'-end sequence of the specific nucleotide sequence in the target RNA; and
(L) a third single-stranded oligonucleotide having a sequence homologous (identical) to the specific nucleotide sequence in the target RNA and is labeled in such a manner that a measurable fluorescence signal is generated when bound to a nucleic acid having the same sequence.

In the above, when the first and second single-stranded oligonucleotides of (A) and (E) are used, the specific nucleotide sequence is a nucleotide sequence moiety.existing in the target RNA, in which its 5'-end starts with the sequence of (3) in the second single-stranded oligonucleotide of (E) and the 3'-end ends with a sequence complementary to the first single-stranded oligonucleotide of (A). Also, when the first and second single-stranded oligonucleotides of (J) and (K) are used, it is a nucleotide sequence moiety existing in the target RNA, in which its 5'-end starts with a sequence identical to the second single-stranded oligonucleotide of (K) and the 3'-end ends with a sequence complementary to the sequence of (3) in the first single-stranded oligonucleotide of (J). Although the specific nucleotide sequence can be decided optionally, it is important that it contains a sequence moiety having such a degree of specificity that the target RNA can be distinguished from other nucleic acids.

The reagent (A) is a first single-stranded oligonucleotide having a complementary sequence that sequence-specifically binds to a specific nucleotide sequence. This reagent complementarily binds to a target RNA, and is used for positioning a sequence complementary to the 3'-end of the specific nucleotide sequence on the 5'-end of a cDNA when the cDNA is synthesized by the RNA-dependent DNA polymerase using the target RNA as a template in the presence of the following reagents (B) and (C).

The reagent (B) is an RNA-dependent DNA polymerase, and the reagent (C) is deoxyribonucleoside triphosphate which is its substrate. A cDNA having on its 5'-end a sequence complementary to the 3'-end of the specific nucleotide sequence in the target RNA is synthesized in the presence of the reagents (A) to (C). This cDNA forms a DNA-RNA double-strand with the target RNA used as a template.

The reagent (D) is ribonuclease H having an activity of digesting the RNA in the DNA-RNA double-stranded form, but an enzyme having an equivalent RNA hydrolyzing activity can also be used. Since reverse transcriptases represented by an avian myoblastoma virus reverse transcriptase (hereinafter referred to as "AMV reverse transcriptase") has an activity of cleaving the RNA in the DNA-RNA double-stranded form, such enzymes can be exemplified.

The reagent (E) is a second single-stranded oligonucleotide having (1) a promoter sequence of a DNA-dependent RNA polymerase, (2) an enhancer sequence of the promoter, and (3) a nucleotide sequence identical to the 5'-end sequence of the specific nucleotide sequence, in this order from the 5'-end side. In the second oligonucleotide, the moiety (3) binds to the 3'-end of cDNA synthesized in the presence of the reagents (A) to (D). Consequently, in the presence of the reagents (C) and (F), respective complementary chains are synthesized by the DNA-directed DNA polymerase from the 3'-end of the second oligonucleotide using the cDNA as a template and at the same time from the 3'-end of the cDNA using the second oligonucleotide, and thus a complete double-stranded DNA having a transcriptable promoter sequence is synthesized.

The reagent (F) is a DNA-directed DNA polymerase. Since a reverse transcriptase typified by AMV reverse transcriptase has the DNA-directed DNA polymerase activity, such a type of enzyme may be used.

The reagent (G) is a DNA-dependent RNA polymerase, and the reagent (E) is ribonucleoside triphosphate which is used as its substrate. The double-stranded DNA synthesized in the presence of the reagents (C), (E) and (F) has a promoter region of the DNA-dependent RNA polymerase on its end. Accordingly, in the presence of the reagents (G) and (H), synthesis of a single-stranded RNA comprising the specific nucleotide sequence is started immediately after the DNA synthesis. Examples of the DNA-dependent RNA polymerase of the reagent (G) include T7 RNA polymerase, T3 RNA polymerase, SP6 RNA polymerase, and the like.

The single-stranded RNA synthesized in the presence of the reagents (G) and (H) is an RNA comprising the specific nucleotide sequence. Accordingly, as a result that they are synthesized and the reagents (A) to (F) are present, a series of the above reactions are generated repeatedly. Thus, in the present invention, a double-stranded DNA having a promoter region on its end is synthesized based on an extremely small amount of a target RNA existing in a sample and becomes the source for synthesizing a single-stranded RNA comprising a specific nucleotide sequence The thus synthesized single-stranded RNA contributes to synthesis of a new double-stranded DNA and, as a result, the amount of the single-stranded RNA comprising the specific nucleotide sequence sharply increases with the lapse of time.

The reagent (I) is a third single-stranded oligonucleotide which has a sequence complementary to the specific nucleotide sequence and is labeled in such a manner that a measurable fluorescence signal is generated when bound, to a nucleic acid having the same sequence. The third single-stranded oligonucleotide may be, for example, a DNA fragment to which an intercalating fluorochrome is bound. For specific assay of the specific nucleotide sequence, the DNA moiety has preferably from 6 to 100 nucleotides, more preferably from 10 to 30 nucleotides. As a matter of course, it is important that the DNA moiety is a sequence which is present in the specific nucleotide sequence and complementary to a sequence moiety that can be 'sufficiently distinguished from nucleic acids other than the target nucleic acid.

In order to prevent elongation of the DNA moiety from its 3'-end by the action of the RNA-dependent DNA polymerase of the reagent (C) which has been already added when it forms a complementary bond with the synthesized single-stranded RNA comprising the specific nucleotide sequence, it is preferred that a sequence non-complementary to the specific nucleotide sequence is added to the 3'-end or that the 3'-end is chemically modified.

When the DNA moiety forms a complementary bond with other nucleic acid, the intercalating fluorochrome intercalates into the double-stranded moiety to change its fluorescence characteristic. An example effective for this purpose is to bind the intercalating fluorochrome to the DNA via a linker having such an appropriate molecular length that does not inhibit its intercalation into the double-stranded moiety. Such a linker is not particularly limited, so long as it is a molecule which does not inhibit intercalation of the intercalating fluorochrome into the double-stranded moiety. A linker molecule selected from bifunctional hydrocarbons having functional groups on both ends is particularly preferred due to convenience in carrying out modification of the oligonucleotide. Additionally, a commercially available reagent set (C6-Thiolmodifier, trade name, manufactured by Clontech) or the like may also be used.

The intercalating fluorochrome is not particularly limited, so long as its fluorescence characteristic is changed by its intercalation into the double-stranded moiety, such as fluctuation of the generated fluorescence wavelength, but those having a property of increasing the fluorescence intensity by intercalation are particularly preferred, for example, from the viewpoint of easy measurement etc. More specifically, preferred examples include thiazole orange, oxazole yellow, and derivatives thereof, which show particularly significant changes in fluorescence intensity.

The position of DNA to which the intercalating fluorochrome is bound via a linker, such as the 5'-end, the 3'-end or a central part, is not particularly limited, so long as intercalation of the intercalating fluorochrome into the double-stranded moiety is not inhibited and a complementary bond of the DNA moiety with RNA is not inhibited.

The amount of the single-stranded RNA synthesized by the reagents (G) and (H) using the double-stranded DNA having a promoter sequence as a template increases with time. It has been confirmed that in this reaction system, the fluorescence intensity increases in proportion to the amount of the synthesized RNA in the presence of the reagent (I) having the property described above and having a sequence complementary to a certain sequence of the single-stranded RNA (*Igaku-no Ayumi*, 184(3): 239–244 (1998); *Nucleic Acid Research*, 24(24): 4992–4997 (1996)).

The reagent (I) coexists with at least the reagents (A) to (H) in a sample expected to contain the target RNA, and the increased single-stranded RNA comprising the specific nucleotide sequence is measured as a fluorescence signal. Also, it has been revealed that, even when the synthesized single-stranded RNA forms a complementary bond with the third oligonucleotide of the reagent (I) to generate a fluorescence signal, this RNA functions as the template for the synthesis of the DNA in the presence of the reagents (A) to (C). Thus, according to the present invention, a series of phenomena, namely synthesis of cDNA, synthesis of double-stranded DNA and synthesis of RNA from the double-stranded DNA under coexisting conditions of respective reagents, are generated in the presence of the third oligonucleotide, and the fluorescence intensity increases in proportion to the increased RNA.

An embodiment in which a combination of the first, second and third single-stranded oligonucleotides of the reagents (J) to (L) is used instead of the combination of the first to third single-stranded oligonucleotides of the reagents (A), (E) and (I) is described below.

The reagent (J) is a first single-stranded oligonucleotide having (1) a promoter sequence of a DNA-dependent RNA polymerase, (2) an enhancer sequence of the promoter, and (3) a sequence complementary to a 3'-end sequence of the specific nucleotide sequence in the target RNA, in this order from the 5'-end side. The moiety (3) of this reagent complementarily binds to the 3'-end of the specific nucleotide sequence, and the cDNA complementary to the target RNA is synthesized in the presence of the reagents (B), (C) and (D) similar to the embodiment using the reagent (A).

The reagent (K) is a single-stranded oligonucleotide having a sequence homologous to the 5'-end of the specific nucleotide sequence in the target RNA. The reagent (K) binds complementarily to the 3'-end of the specific nucleotide sequence of cDNA, and then a double-stranded DNA having the promoter sequence of the RNA polymerase is synthesized in the presence of the reagents (C) and (F). Subsequently, a second single-stranded RNA complementary to the specific nucleotide sequence is synthesized from the double-stranded DNA in the presence of the reagents (G) and (H).

Thereafter, the 3'-end of the second RNA binds complementarily to the reagent (K), and a second CDNA correspondin to the second RNA is synthesized in the presence of the reagents (B) to (D). The 3'-end of the second cDNA complementarily binds to the moiety (3) of the reagent (J), a double-stranded DNA containing a promoter sequence is synthesized by the reagents (C) and (F), and the second RNA is synthesized by the reagents (G) and (H). The thus synthesized second RNA complementary to the specific nucleotide sequence becomes the source for synthesizing a new double-stranded DNA to generate a series of reactions repeatedly and, as a result, the amount of the second RNA sharply increases.

The thus obtained second RNA has a sequence complementary to the specific nucleotide sequence in the target RNA. When the reagent (L) as a third single-stranded oligonucleotide which has a sequence identical to the specific nucleotide sequence and is labeled with an intercalating fluorochrome is allowed to coexist, the fluorescence intensity increases in proportion to the amount of the thus synthesized second RNA.

Additionally, according to the present invention, it is possible to assay a DNA containing a specific nucleotide sequence and is originally present in the sample. The reason for this is that, when a double-stranded DNA having a transcriptable promoter sequence is prepared by a known method and used as a target nucleic acid, the double-stranded DNA can be used as a template of the amplification reaction so that the RNA transcription product can be formed in the presence of a RNA polymerase. Examples of the method for preparing the double-stranded DNA having a transcriptable promoter sequence include a method in which a promoter sequence is added to a target DNA using a promoter primer and a DNA polymerase and a method in which a DNA chain having a promoter sequence is bound to a target DNA using a DNA ligase.

Preferably, the measurement of the fluorescence signal according to the present invention is carried out with time immediately after the addition of the reagents (A) to (I) or after a predetermined lapse of time of the addition. The third DNA of the reagent (I) repeats bonding and dissociation with the synthesized RNA. However, since the fluorescence signal measured at the time of bonding reflects the existing amount of the RNA at the time of each measurement, it is possible to trace increasing conditions of the single-stranded RNA with time. Also, the measurement per se may be either continuous or intermittent at predetermined intervals. Furthermore, the apparatus for measuring the fluorescence signal does not constitute a part of the present invention, but any apparatus which can measure the fluorescence signal in at least one reaction tube continuously or intermittently at predetermined intervals may be used.

The measuring period of the fluorescence signal includes a period during which a significant difference can be found between the increasing period of the fluorescence intensity of a test plot containing a certain amount of the target RNA and that of a test plot which is free of the target RNA, namely a period until the fluorescence intensity of the test plot containing a certain amount of the target RNA becomes almost constant, which is generally 4 hours, preferably 1 hour.

From a relationship between a passing time of the amplification reaction and an increase in the fluorescence intensity in the amplification and periodical fluorescence intensity measuring steps, a time which satisfies a prescribed criterion is calculated and the initial RNA amount is determined from the thus calculated time, based on a phenomenon that the fluorescence intensity increasing time delays at a certain rate as the target RNA originally existing in the sample (initial RNA amount) decreases.

An example of the time which satisfies a prescribed criterion to be used herein is a time which reaches a certain fluorescence increasing rate (fluorescence intensity value at a predetermined time fluorescence intensity value of background) when compared with the control plot which is free of the target RNA or a time at which significant increase in the fluorescence intensity is not observed at the initial stage of the RNA amplification step. More specifically, a time which exceeds three-fold of the standard deviation of fluorescence increasing rates of a plurality of control plots which are free of the target RNA at a predetermined time can be used. Also useful is a time when, in a relationship between the common logarithm of the fluorescence intensity rate and the time, the common logarithmic value of the fluorescence intensity rate significantly increases in comparison with the control plot.

Additionally, a time calculated by a certain criterion can also be determined using a time when a fluorescence intensity rate per unit time in the fluorescence intensity rate becomes a maximum. Also, as an easily conceivable application example of this assay method, it is possible to analyze the fluorescence intensity rate and the time by carrying out mathematical treatments, such as differentiation, logarithmic expression, approximate curve, and the like. Additionally, the initial RNA amount may be determined by comparing the calculated time with the case of at least two samples having a different known concentration.

As apparent from the entire descriptions, according to the present invention, the amount of a target RNA (single-stranded RNA) containing a specific nucleotide sequence contained in the sample and originally existing in a sample can be assayed at an almost constant temperature by only one step of a manual operation carried out at the time of the commencement of the reaction and quickly.

In the present invention, a double-stranded DNA having a DNA-dependent RNA polymerase promoter region on its end is synthesized based on a target RNA in a sample and becomes the source for synthesizing a large amount of a single-stranded RNA, and the amount of the synthesized single-stranded RNA is sharply increased so that the initial RNA amount can be determined conveniently and quickly by analyzing the increasing process of fluorescence intensity in a step in which increase in the fluorescence due to a complementary bond of a probe labeled with an intercalating fluorochrome to the formed single-stranded RNA is measured.

Additionally, not only viral RNA in the field of clinical diagnosis but also microorganisms in food and soil including, for example, pathogenic bacteria and antibiotics-resistant bacteria can be assayed by merely changing sequences of the first to third oligonucleotides.

The present invention will be described in detail based on the following examples, but the present invention is not restricted by these examples.

EXAMPLE 1

Relating to human hepatitis C virus RNA, a calibration curve was prepared for determining RNA originally existing in samples.

(1) A portion of the nucleotide numbers 113 to 267 of human hepatitis C virus RNA (Kato et al., *Proc. Natl. Sci., USA*, 87: 9524–9528, (1990)) was used as a standard RNA sample, determined by ultraviolet region absorbance at 260 nm, and then diluted with the following RNA diluent to give a concentration of $10^9$, $10^8$, $10^7$, $10^6$, $10^5$ or $10^4$ copies/4 μl. The diluent alone is used as a control test plot.

Composition of RNA diluent:
10 mM Tris-HCl (pH 8.0)
0.1 mM EDTA (2) A reaction solution having the following composition of 21.2 μl was dispensed into 0.5 ml capacity tubes for PCR (Gene Amp Thin-Walled Reaction Tubes, manufactured by Perkin-Elmer), 4 μl of the RNA sample was added thereto, and then 50 μl of mineral oil was over-layered.

Composition of reaction solution (each concentration in 30 μl of a final reaction solution volume):

60 mM Tris-acetate buffer (pH 8.1);
13.5 mM magnesium acetate;
120 mM potassium acetate;
16% sorbitol;
10 nM DDT;
0.5 mM of each of dATP, dCTP, dGTP and dTTP;
1 mM of each of ATP, CTP, GTP and UTP;
1.25 mM of ITP;
0.2 μM of the first oligonucleotide
(Sequence (SEQ ID NO:1)) 5'-GCCTTTCGCGACCCAACA-3';
0.2 μM of the second oligonucleotide having SP6 promoter sequence
(Sequence (SEQ ID NO:2)) 5'-ATTTAGGTGACACTAT AGAATACAACCTCCCGGGAGAGCCATAGTG GTCT-3'
(In this sequence, the "ATTTAGGTGACACTATA" moiety is a SP6 promoter sequence, and the "GA ATA-CAA" moiety is an enhancer sequence);
0.025 μM of the third oligonucleotide labeled with an intercalating fluorochrome
(Sequence (SEQ ID NO:3)) 5'-CTCGC*GGGGGCTG-3'
(The symbol * indicates a labeled position with the intercalating fluorochrome.),
wherein a chemical structure of the intercalating fluorochrome moiety of the third oligonucleotide labeled with an intercalating fluorochrome and used in Example 1 is shown below, and wherein $B_1$ to $B_3$ indicate nucleic acid bases;

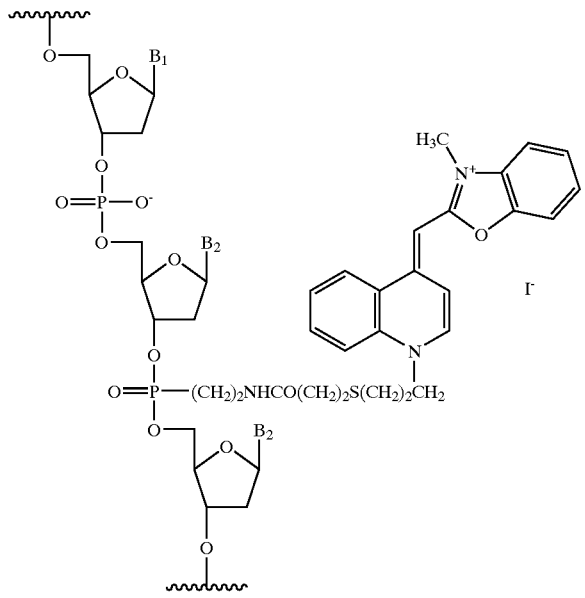

30 units of a ribonuclease inhibitor;
2% of DMSO; and
distilled water for volume adjustmnent (3) After incubation of this reaction solution at 50° C. for 5 minutes, 4.8 μl of an enzyme solution having the following composition was added. Composition of enzyme solution:
42 units of AMV reverse transcriptase (manufactured by Takara Shuzo Co., Ltd.);
171 units of SP6 RNA polymerase (manufactured by Takara Shuzo Co., Ltd.);

3 µg of bovine serum albumin; and distilled water for volume adjustment

Subsequently, using a fluorescence spectrophotometer which is equipped with a temperature controlling means and can measure the PCR tubes directly, the PCR tubes were incubated at 50° C., and the fluorescence intensity of the reaction solution in each tube was measured at an excitation wavelength of 490 nm and a fluorescence wavelength of 510 nm at intervals of 5 minutes.

Fluorescence increasing rates (fluorescence intensity value at a predetermined time÷fluorescence intensity value of background) in respective sample concentrations are shown in FIGS. 1 to 6, wherein the time when the enzyme solution is added is 0 minute. Furthermore, the experiments were conducted five times at respective sample concentrations, and the results are shown by various symbols (e.g., ●, x etc.) in FIGS. 1 to 6.

Figure 7:
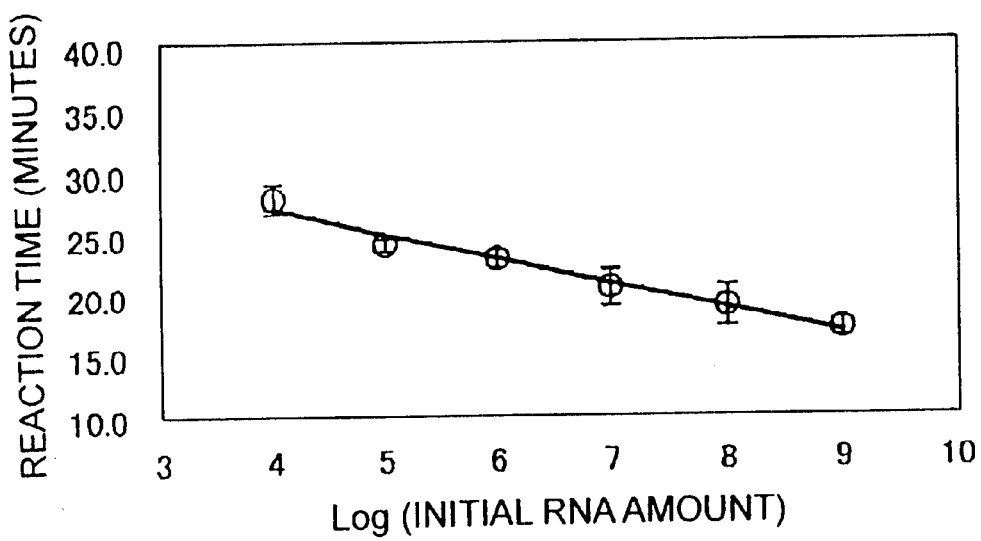
FIG. 7 is a calibration curve prepared from the average time when the fluorescence increasing rate reached 1.2 in a relationship between the reaction time and the fluorescence increasing rate in each sample concentration carried out in Example 1, wherein the error bar indicates ±standard deviation.

Using the zero copy sample consisting of the diluent alone as the control plot, a value obtained by adding three-fold of the standard deviation to the average of fluorescence increasing rates after 60 minutes, namely average of the times when the fluorescence increasing rate reached a value of 1.2, and the regression line by least square are shown in FIG. 7. A line showing good correlation was obtained with a correlation coefficient of −0.990 (y=−2.09x+35.56 (x: abscissa, y: ordinate)). The coefficient of variation in each concentration was 4.4%. by $10^4$ copies, 2.1% by $10^5$ copies, 3.1% by $10^6$ copies, 7.4% by $10^7$ copies, 9.1% by $10^8$ copies, and 4.2% by $10^9$ copies, thus showing a good reproducibility.

Figure 8:
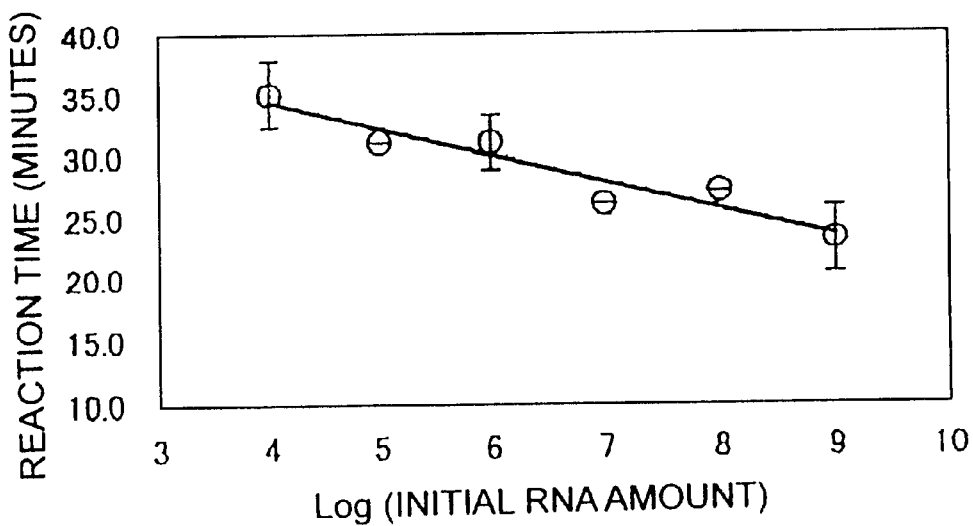
FIG. 8 is a calibration curve prepared from the average time when the fluorescence increasing rate became a maximum in a relationship between the reaction time and the fluorescence increasing rate in each sample concentration carried out in Example 1, wherein the error bar indicates ±standard deviation.

In these fluorescence increasing rates, the average fluorescence increasing rate per unit time, namely a time when a value ((fluorescence increasing rate—fluorescence increasing rate in the preceding measurement)÷measuring interval (5 minutes)) shows a maximum, and the regression line by least square are shown in FIG. 8. The correlation coefficient was −0.955 (y=−2.2x+43.133 (x: abscissa, y: ordinate)), and the coefficient of variation in each concentration was 7.8% by $10^4$ copies, 0% by $10^5$ copies, 7.2% by $10^6$ copies, 0% by $10^7$ copies, 0% by $10^9$ copies, and 11.9% by $10^9$ copies.

Based on these results, it was confirmed that a calibration curve having a good reproducibility can be obtained by this method.

EXAMPLE 2

Using a sample A and a sample B containing a standard RNA, reproducibility and specificity were examined.

Figure 9:
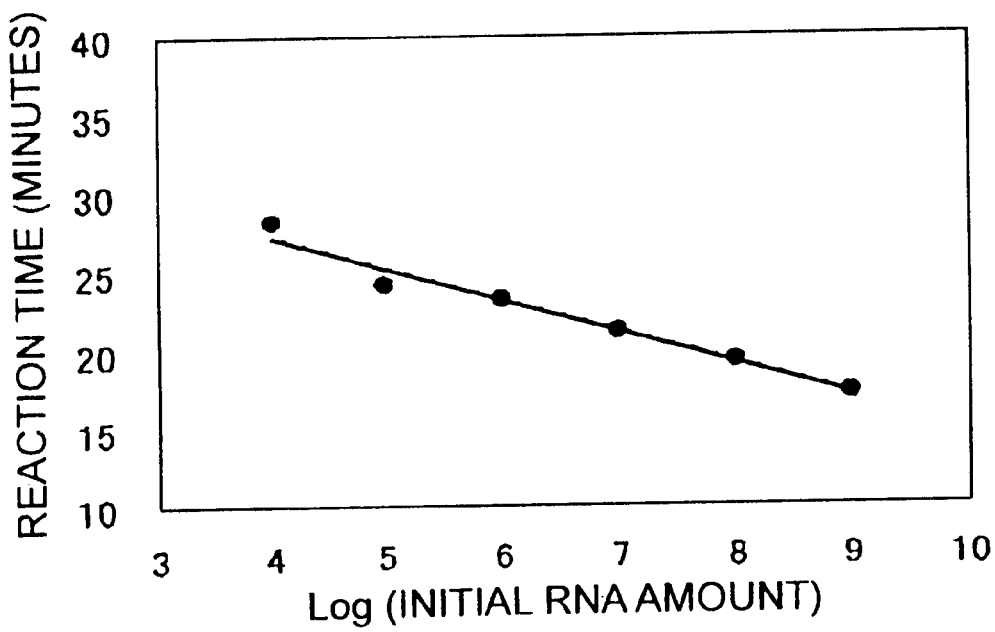
FIG. 9 is a calibration curve prepared from the average time when the fluorescence increasing rate reached 1.2 in a relationship between the reaction time and the fluorescence increasing rate in each sample concentration carried out in Example 2.
Figure 10:
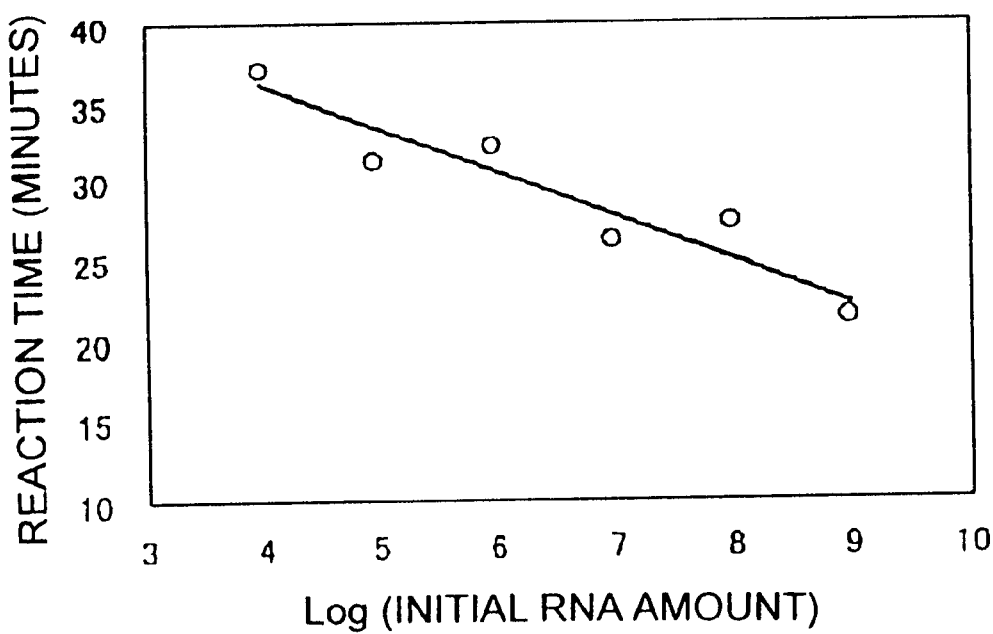
FIG. 10 is a calibration curve prepared from the average time when the fluorescence increasing rate became a maximum in a relationship between the reaction time and the fluorescence increasing rate in each sample concentration carried out in Example 2.

(1) In accordance with the method of Example 1, calibration curves were prepared using a standard RNA of $10^4$ copies to $10^9$ copies. A calibration curve when the time reaching a fluorescence increasing rate of 1.2 is used as a criterion is shown in FIG. 9 (correlation coefficient: −0.987 (y=−2.0571x+35.371 (x: abscissa, y: ordinate)), and a calibration curve when the time of maximum fluorescence increasing rate per unit time is used as a criterion is shown in FIG. 10 (correlation coefficient: −0.944 (y=−2.8x+47.2 (x: abscissa, y: ordinate)).

(2) Using 4 µl of each of the samples A and B containing the standard RNA, the reaction solution and enzyme solution were added in the same manner as in Example 1, each in four cycles, and then incubated at 50° C. to carry out a fluorescence measurement at intervals of 5 minutes. In this case, the samples A and B prepared herein contained $10^5$ copies/4 µl and $10^8$ copies/4 µl, respectively.

(3) The determination results are shown in Table 1 (common logarithm value of the initial RNA amount is expressed as an index value). In the samples A and B, determination results which almost coincided with the theoretical values were obtained. It was able to carry out the determination within an error range of a single figure or less in all test plots, and the reproducibility was also excellent with a coefficient of variation of 5% or less. Based on these results, it was confirmed that the concentration of a specified RNA originally existing in a sample can be determined by this method conveniently and quickly with a good reproducibility.

TABLE 1

| | Test No. | Initial RNA amount obtained from the time reaching a fluorescence increasing rate of 1.2 (index value | Initial RNA amount obtained from the time becoming a maximum fluorescence increasing rate (index value) |
|---|---|---|---|
| Sample A | No. 1 | 5.5 | 5.8 |
| (Theore- | No. 2 | 5.0 | 5.8 |
| tical | No. 3 | 5.5 | 5.8 |
| value: | No. 4 | 5.5 | 5.8 |
| index | Index value average | 5.4 | 5.8 |
| value 5) | Standard deviation | 0.24 | 0 |
| | Coefficient variation | 4.5% | 0% |
| Sample B | No. 1 | 8.4 | 7.2 |
| (Theore- | No. 2 | 8.4 | 7.2 |
| tical | No. 3 | 8.4 | 7.2 |
| value: | No. 4 | 8.0 | 7.2 |
| index | Index value average | 8.3 | 7.2 |
| value 5) | Standard deviation | 0.24 | 0 |
| | Coefficient variation | 2.9% | 0% |

While the invention has been described in detail and with reference to specific embodiments thereof, it will be apparent to one skilled in the art that various changes and modifications can be made therein without departing from the spirit and scope thereof.

This application is based on Japanese patent application No. 11-143854 filed on May 24, 1999, the entire contents of which are incorporated hereinto by reference.

What is claimed is:

1. A method for determining a concentration of a target RNA in a sample consisting of the steps:

providing an RNA amplification system in which:
  (a) a double-stranded DNA is produced using, as a template, a target RNA containing a specific nucleotide sequence in a sample, said double-stranded DNA has a promoter sequence and transcribes an RNA comprising the specific nucleotide sequence or a sequence complementary to the specific nucleotide sequence;
  (b) an RNA transcription product comprising the specific nucleotide sequence or a sequence complementary to the specific nucleotide sequence is produced in the presence of an RNA polymerase; and
  (c) the double-stranded DNA is produced using the RNA transcription product as a template,
  wherein said steps (a), (b) and (c) are carried out in the presence of a probe labeled with an intercalating fluorochrome having a sequence complementary to the RNA transcription product, measuring the fluorescence intensity in the RNA amplification system with time;

calculating a time when the fluorescence intensity satisfies a prescribed criterion based on the measured change in the fluorescence intensity with time; and determining a concentration of the target RNA in the sample based on the calculated time, wherein all steps of:
  production of a double-stranded DNA using a target RNA;
  production of an RNA transcription product from the double-stranded DNA;
  measurement of the RNA transcription product using a probe; and
  production of the above double-stranded using the RNA transcription product;
are carried out continuously.

2. The method according to claim 1, wherein the time which satisfies a prescribed criterion is a time to reach a definite fluorescence intensity.

3. The method according to claim 1, wherein the time which satisfies a prescribed criterion is a time when an increasing rate of the fluorescence intensity per unit of time becomes a maximum.

4. The method according to claim 1, wherein the concentration of the target RNA is determined by comparing the time which satisfies a prescribed criterion with the times in at least two RNA samples containing the specific nucleotide sequence at a different concentration.

5. The method according to claim 2, wherein the concentration of the target RNA is determined by comparing the time which satisfies a prescribed criterion with the times in at least two RNA samples containing the specific nucleotide sequence at a different concentration.

6. The method according to claim 3, wherein the concentration of the target RNA is determined by comparing the time which satisfies a prescribed criterion with the times in at least two RNA samples containing the specific nucleotide sequence at a different concentration.

7. The method according to claim 1, wherein, in the RNA amplification system,
  a single-stranded DNA is produced in the presence of an RNA-dependent DNA polymerase using a primer having a sequence. complementary to the specific nucleotide sequence and a primer having a homologous sequence of the specific nucleotide sequence, wherein one of the primers is a promoter primer having a promoter sequence of the RNA polymerase at the 5'-side, and using the target RNA as the template;
  the double-stranded DNA is produced in the presence of a DNA-dependent DNA polymerase using the single-stranded DNA as a template;

the RNA transcription product is produced from the double-stranded DNA in the presence of an RNA polymerase; and the RNA transcription product is subsequently used as the template for producing the single-stranded DNA in the presence of the RNA-dependent DNA polymerase.

8. The method according to claim 1, wherein the probe labeled with an intercalating fluorochrome is complementary to the RNA transcription product so that the intercalating fluorochrome is intercalated between the produced RNA and the probe.

9. The method according to claim 1, wherein a complex formed by a complementary bond between the probe labeled with an intercalating fluorochrome and the RNA transcription product has a fluorescence characteristic that differs from that of probe molecules that have not formed a complex with the RNA transcription product.

10. The method according to claim 9, wherein the probe labeled with an intercalating fludrochrome is complementary to the RNA transcription product so that the intercalating fluorochrome is intercalated between the produced RNA and the probe.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:

-continued

```
<223> OTHER INFORMATION: Description of Artificial Sequence:First
      oligonucleotide

<400> SEQUENCE: 1
gcctttcgcg acccaaca                                                 18

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:Second
      oligonucleotide

<400> SEQUENCE: 2
atttaggtga cactatagaa tacaacctcc cgggagagcc atagtggtct              50

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:Third
      oligonucleotide

<400> SEQUENCE: 3
ctcgcggggg ctg                                                      13
```